United States Patent

Bedekovic et al.

[11] Patent Number: 4,587,539
[45] Date of Patent: May 6, 1986

[54] CHROMOGENIC DIHYDROFUROPYRIDINONES

[75] Inventors: Davor Bedekovic, Therwil; Ian J. Fletcher, Magden, both of Switzerland

[73] Assignee: Ciba-Geigy Corporation, Ardsley, N.Y.

[21] Appl. No.: 690,075

[22] Filed: Jan. 9, 1985

Related U.S. Application Data

[60] Division of Ser. No. 502,035, Jun. 7, 1983, Pat. No. 4,508,897, which is a continuation-in-part of Ser. No. 449,955, Dec. 15, 1982.

[30] Foreign Application Priority Data

Dec. 23, 1981 [CH] Switzerland ............. 8250/81
Dec. 23, 1981 [CH] Switzerland ............. 8251/81
Apr. 7, 1983 [CH] Switzerland ............. 1868/83

[51] Int. Cl.$^4$ .................. B41M 5/16; B41M 5/18; B41M 5/22
[52] U.S. Cl. .................... 346/220; 346/223; 427/151
[58] Field of Search .............. 346/220, 223, 204, 214, 346/215, 217, 218, 226; 427/150–152

[56] References Cited

U.S. PATENT DOCUMENTS 3,936,564  2/1976  Miyazawa et al. ........... 346/220
4,480,002 10/1984  Asano et al. ............... 346/221

FOREIGN PATENT DOCUMENTS 49-118515 11/1974  Japan ..................... 346/220
2103234A  2/1983  United Kingdom ........... 346/220

*Primary Examiner*—Bruce H. Hess
*Attorney, Agent, or Firm*—Edward McC. Roberts; Kevin T. Mansfield

[57] ABSTRACT

Chromogenic azaphthalides of the formula

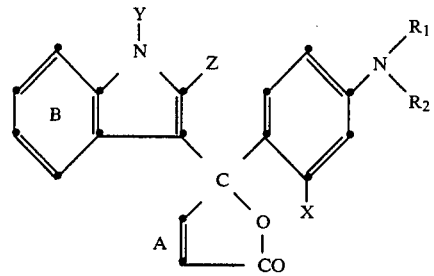

wherein $R_1$ and $R_2$ independently of each other are hydrogen, $C_1$–$C_{12}$ alkyl which is unsubstituted or substituted by halogen, hydroxyl, cyano or lower alkoxy, or are cycloalkyl, benzyl or phenyl, or benzyl or phenyl which are substituted by halogen, nitro, cyano, lower alkyl, lower alkoxy or lower alkoxycarbonyl; or $R_1$ and $R_2$ together with the nitrogen atom to which they are attached are a 5-membered or 6-membered heterocyclic radical and in particular pyrrolidinyl;

X is hydrogen, halogen, lower alkyl, lower alkoxy, benzyl, phenyl, benzyloxy, phenoxy, or benzyl or benzyloxy which are substituted by halogen, nitro, lower alkyl or lower alkoxy;

Y is $C_6$–$C_9$ alkyl;

Z is hydrogen, lower alkyl or phenyl; and the ring A is a pyridine radical and the benzene nucleus B is unsubstituted or substituted by halogen, nitro, cyano, lower alkyl, lower alkoxy, lower alkoxycarbonyl, amino, lower alkylamino or di-(lower alkyl)-amino as well as a novel process for the preparation of 4-azaphthalides.

The azaphthalides are useful color formers for pressure-sensitive or heat-sensitive recording materials and produce, in particular, strong, lightfast blue colorations.

13 Claims, No Drawings

CHROMOGENIC DIHYDROFUROPYRIDINONES

CROSS REFERENCE

This is a division of application Ser. No. 502,035, filed 6/7/83, now U.S. Pat. No. 4,508,897, which in turn is a continuation-in-part of application Ser. No. 449,955, filed 12/15/82.

The present invention relates to chromogenic azaphthalides (=dihydrofuropyridinones), to processes for their preparation, and to their use as colour formers in pressure-sensitive or heat-sensitive recording materials.

The chromogenic azaphthalides of this invention have in particular the general formula

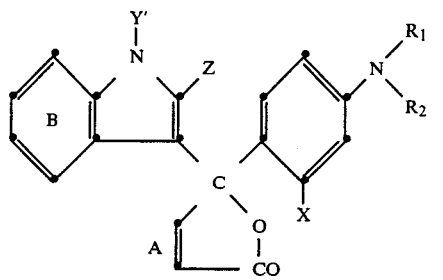

wherein $R_1$ and $R_2$ independently of each other are hydrogen, $C_1$–$C_{12}$-alkyl which is unsubstituted or substituted by halogen, hydroxyl, cyano or lower alkoxy, or are cycloalkyl, benzyl or phenyl, or benzyl or phenyl which are substituted by halogen, nitro, cyano, lower alkyl, lower alkoxy or lower alkoxycarbonyl; or $R_1$ and $R_2$ together with the nitrogen atom to which they are attached are pyrrolidinyl;

X is hydrogen, halogen, lower alkyl, lower alkoxy, benzyl, phenyl, benzyloxy, phenoxy, or benzyl or benzyloxy which are substituted by halogen, nitro, lower alkyl or lower alkoxy;

Y' is $C_6$–$C_9$alkyl;

Z is hydrogen, lower alkyl or phenyl; and the ring A is a pyridine radical and the benzene nucleus B is unsubstituted or substituted by halogen, nitro, cyano, lower alkyl, lower alkoxy, lower alkoxycarbonyl, amino, lower alkylamino or di-(lower alkyl)-amino.

In the definition of the radicals of the azaphthalides, the term "lower" qualifying alkyl and alkoxy groups will normally be understood to denote groups which contain 1 to 5, preferably 1 to 3, carbon atoms. Examples of lower alkyl groups are methyl, ethyl, n-propyl, isopropyl, n-butyl, sec-butyl or amyl, and examples of lower alkoxy groups are methoxy, ethoxy or isopropoxy.

$R_1$ and $R_2$ as alkyl groups may be straight chain or branched alkyl groups, e.g. methyl, ethyl, n-propyl, isopropyl, n-butyl, sec-butyl, amyl, n-hexyl, 2-ethylhexyl, n-heptyl, n-octyl, iso-octyl, n-nonyl, isononyl or n-dodecyl.

$R_1$ and $R_2$ as substituted alkyl groups are in particular cyanoalkyl, haloalkyl, hydroxyalkyl, alkoxyalkyl, each containing preferably a total of 2 to 4 carbon atoms, e.g. β-cyanoethyl, β-chloroethyl, β-hydroxyethyl, β-methoxyethyl or β-ethoxyethyl.

$R_1$ and $R_2$ as cycloalkyl may be cyclopentyl or, preferably, cyclohexyl.

Preferred substituents in the benzyl moiety of the radicals R and X, in the phenyl moiety of the radicals $R_1$ and $R_2$ and in the benzyloxy moiety of the radical X are e.g. halogens, nitro, methyl or methoxy. Examples of such araliphatic and aromatic radicals are p-methylbenzyl, o- or p-chlorobenzyl, o- or p-nitrobenzyl, o- or p-tolyl, xylyl, o-, m- or p-chlorophenyl, o- or p-nitrophenyl, o- or p-methoxyphenyl, chlorobenzyloxy or methylbenzyloxy.

The substituents $R_1$ and $R_2$ can be different, but are preferably identical. Preferably, $R_1$ and $R_2$ are benzyl or, most preferably, lower alkyl, especially methyl or ethyl. $R_1$ and $R_2$ together with the nitrogen atom to which they are attached can form a pyrrolidinyl radical, which is also a preferred substituent. $R_1$ is advantageously also cyclohexyl.

X may be with advantage hydrogen, halogen, lower alkyl, e.g. methyl; or benzyloxy or lower alkoxy, e.g. methoxy, ethoxy, isopropoxy or tert-butoxy. X is preferably hydrogen, benzyloxy or lower alkoxy, and is most preferably ethoxy.

An alkyl radical Y' may be n-hexyl, 2-ethylhexyl, n-heptyl, n-octyl, isooctyl, tert-octyl, n-nonyl or isononyl. The N-substituent Y' is preferably $C_6$–$C_8$alkyl, e.g. n-hexyl, n-heptyl or, most preferably n-octyl. Z is preferably phenyl or, most preferably, methyl.

The nitrogen atom of the pyridine ring A is advantageously in the ortho-position to the carbonyl group or in the ortho-position to the linking carbon atom of the furan ring. The chromogenic azaphthalides of the formula (1) are preferably mixtures of isomers of 4-azaphthalides (=7,7-disubstituted 5,7-dihydrofuro-5-pyridinones) and 7-azaphthalides (=5,5-disubstituted 5,7-dihydrofuro-7-pyridinones), in which the nitrogen atoms of the pyridine ring are in the ortho-positions specified above. The ring B is preferably not further substituted or may also be substituted by halogen.

Interesting chromogenic azaphthalides are those of the formula

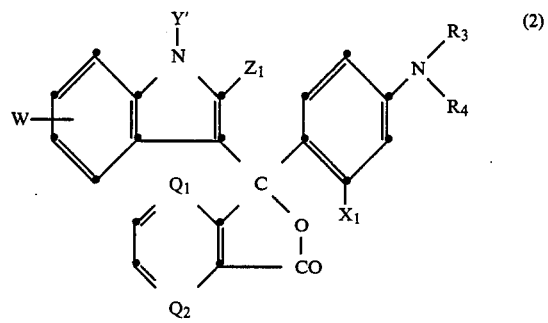

wherein $R_3$ and $R_4$ independently of each other are lower alkyl, benzyl, or benzyl which is substituted by halogen, methyl or methoxy, or $R_3$ and $R_4$ together with the nitrogen atom to which they are attached are pyrrolidinyl; one of $Q_1$ and $Q_2$ is nitrogen and the other is CH, $X_1$ is hydrogen, lower alkoxy or benzyloxy; Y' is $C_6$–$C_9$alkyl; $Z_1$ is lower alkyl or phenyl; and W is hydrogen or halogen.

Halogen in connection with the above substituents in formulae (1) and (2) denotes e.g. fluorine, bromine or preferably chlorine.

Preferred azaphthalides of the formula (2), which are obtained preferably in the form of mixtures of isomers, are those in which $X_1$ is lower alkoxy and Y' is $C_6$–$C_8$alkyl, in particular n-octyl. $R_3$ and $R_4$ are preferably lower alkyl.

Particularly interesting mixtures of isomers are those of azaphthalides of the formula

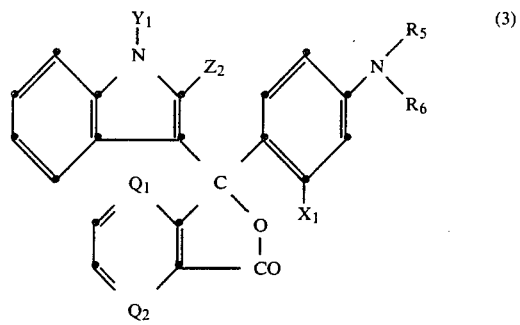

(3)

wherein each of $R_5$ and $R_6$ is lower alkyl or benzyl, or $R_5$ and $R_6$ together with the nitrogen atom to which they are attached are pyrrolidinyl; one of $Q_1$ and $Q_2$ is N and the other is CH; $X_1$ is hydrogen, benzyloxy or lower alkoxy, preferably ethoxy; $Z_2$ is methyl or phenyl; and $Y_1$ is $C_6$–$C_8$alkyl, preferably, n-hexyl or, most preferably, n-octyl.

Particularly preferred compounds of the formula (3) are those in which $R_5$ and $R_6$ are methyl or ethyl, or $R_5$ and $R_6$ together with the nitrogen atom to which they are attached are pyrrolidinyl, and $X_1$ is ethoxy, $Z_2$ is methyl and $Y_1$ is n-octyl.

The azaphthalides of the formulae (1) to (3) are novel compounds. One process for the preparation of the azaphthalides of the formula (1) comprises reacting a compound of the formula

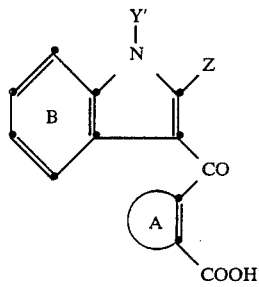

(4)

with a compound of the formula

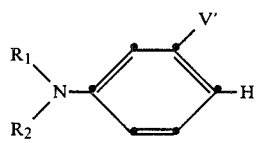

(5)

in which formulae above A, B, Y', Z, $R_1$ and $R_2$ have the meanings previously assigned to them and V' has the meaning of X or is hydroxy, and subsequently alkylating or aralkylating the reaction product if V' is hydroxy.

Alternatively, the azaphthalides of the invention may also be prepared by reacting a compound of the formula

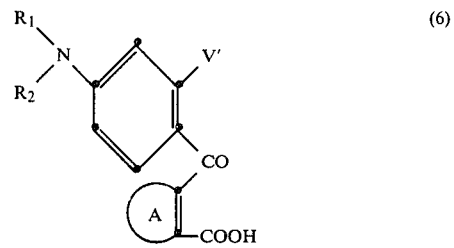

(6)

with an indole of the formula

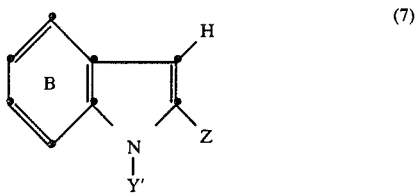

(7)

in which formulae above A, B, $R_1$, $R_2$, Y' and Z have the meanings previously assigned to them and V' has the meaning of X or is hydroxy, and subsequently alkylating or aralkylating the reaction product if V' is hydroxy.

The above processes are preferably carried out by reacting the reaction components in the presence of an acid condensing agent in the temperature range from 20° to 80° C. Examples of such condensing agents are acetic anhydride, sulfuric acid, phosphoric acid and phosphoroxy chloride.

The alkylation or aralkylation of the reaction products in which V' is hydroxy, is ordinarily carried out by known methods. For example, the reaction is carried out in the presence of an acid acceptor, e.g. an alkali metal carbonate, or a tertiary nitrogen base such as triethylamine, and optionally in the presence of an inert organic solvent such as acetone, isopropyl alcohol, chlorobenzene or nitrobenzene. Suitable alkylating agents are alkyl halides such as methyl iodide, ethyl iodide, methyl chloride or ethyl chloride, or dialkyl sulfates such as dimethyl sulfate or diethyl sulfate. Suitable aralkylating agents are in particular benzyl chloride and the corresponding substitution products, e.g. p-chlorobenzyl chloride or 2,4-dimethylbenzyl chloride, which are preferably used in a non-polar organic solvent such as benzene, toluene or xylene.

The starting materials of the formulae (4) and (6) are normally obtained by reacting an anhydride of the formula

(8)

with a compound of the formula (7) or with a compound of the formula (5), said reaction being carried out, if desired, in an organic solvent and optionally in the presence of a Lewis acid, e.g. aluminium chloride. Examples of suitable organic solvents are: dimethylformamide, acetonitrile, lower aliphatic carboxylic acids such as acetic acid; and benzene, toluene, xylene or chlorobenzene. It is preferred to carry out the reaction in the temperature range from 15° C. to the boiling point of the solvent employed. Without being isolated, the resultant compounds of the formula (4) may be further used for the reaction with the aniline compounds of the formula (5). The compounds of the formula (6), wherein V' is alkoxy or benzyloxy, are preferably obtained by conventional alkylation or aralkylation of the intermediate obtained by reacting an anhydride of the formula (8) with an aniline compound of the formula (5), wherein V' is hydroxy. The alkylating and aralkylating agents may be the same as those indicated for the preparation of the compounds of the formulae (1) to (3).

The azaphthalides of the formulae (1) to (3) are normally colourless or, at most, faintly coloured. When these colour formers are brought into contact with an acid developer, e.g. an electron acceptor, they produce intense greenish blue, blue or violet blue shades of excellent fastness to sublimation and light. They are therefore also very useful when mixed with one or more other known colour formers, for example 3,3-(bis-aminophenyl)-phthalides, 3,3-(bis-indolyl)-phthalides, 3-aminofluoranes, 2,6-diaminofluoranes, leucoauramines, spiropyranes, spirodipyranes, chromenoindoles, phenoxazines, phenothiazines, carbazolylmethanes or triarylmethane-leuco dyes, to give blue, navy blue, grey or black colorations.

The azaphthalides of the formulae (1) to (3) exhibit both on clays and especially on phenolic substrates an improved colour intensity and lightfastness. They are suitable in particular as rapidly developing colour formers for use in a heat-sensitive or especially in a pressure-sensitive recording material which can also be a copying material.

A pressure-sensitive material consists, for example, of at least one pair of sheets which contain at least one colour former of the formulae (1) to (3) dissolved in an organic solvent, and a solid electron acceptor as developer.

Typical examples of such developers are activated clays such as attapulgite, acid clay, bentonite, montmorillonite, activated clay, e.g. acid-activated bentonite or montmorillonite, and also zeolith, halloysite, silica, alumina, aluminium sulfate, aluminium phosphate, zinc chloride, activated kaolin or any clay. Preferred developers are acidic organic compounds, for example unsubstituted or ring-substituted phenols, salicylic acid or salicylates and their metal salts, or an acidic polymer, for example a phenolic polymer, an alkylphenolacetylene resin, a maleic acid/rosin resin or a partially or completely hydrolysed polymer of maleic acid and styrene, ethylene or vinyl methyl ether, or carboxypolymethylene. Mixtures of these polymers can also be used. Particularly preferred developers are zinc salicylates or the condensation products of p-substituted phenols with formaldehyde. These latter may also contain zinc.

The developers may also be used with other basically inert or almost inert pigments or further auxiliaries such as silica gel, or UV-absorbers such as 2-(2-hydroxyphenyl)-benztriazoles. Examples of such pigments are: talcum, titanium dioxide, zinc oxide, chalk, clays such as kaolin, as well as organic pigments, e.g. urea/formaldehyde condensates (BET surface area 2-75 g/m$^2$) or melamine/formaldehyde condensates.

The colour former effects a coloured marking at those points where it comes into contact with the electron acceptor. In order to prevent the colour formers contained in the pressure-sensitive recording material from becoming active prematurely, they are usually separated from the electron acceptor. This separation can conveniently be accomplished by incorporating the colour formers in foamlike, spongelike or honeycomblike structures. The colour formers are preferably encapsulated in microcapsules, which as a rule can be ruptured by pressure.

When the capsules are ruptured by pressure, for example with a pencil, the colour former solution is transferred to an adjacent sheet which is coated with an electron acceptor and a coloured area is thus produced. This colour results from the dye which is formed and which is adsorbed in the visible range of the electromagnetic spectrum.

The colour formers are encapsulated preferably in the form of solutions in organic solvents. Examples of suitable solvents are preferably non-volatile solvents, for example a polyhalogenated paraffin, such as chloroparaffin, or a polyhalogenated diphenyl, such as monochlorodiphenyl or trichlorodiphenyl, and also tricresyl phosphate, di-n-butyl phthalate, dioctyl phthalate, trichlorobenzene, trichloroethylphosphate, an aromatic ether such as benzylphenyl ether, a hydrocarbon oil such as paraffin or kerosene, an alkylated (e.g. with isopropyl, isobutyl, sec- or tert-butyl) derivative of diphenyl, naphthalene or triphenyl; dibenzyl toluene, terphenyl, partially hydrogenated terphenyl, a monobenzylated and/or dibenzylated xylene, a mono- to tetramethylated diphenylalkane, e.g. bis-tolylethane or bis-xylylethane, 1-isopropylphenyl-2-phenylethane or bis-(isopropylphenyl)ethane; or other chlorinated or hydrogenated, condensed aromatic hydrocarbons. Mixtures of different solvents, especially mixtures of paraffin oils or kerosene and diisopropylnaphthalene or partially hydrogenated terphenyl, are often used in order to obtain an optimum solubility for the colour formation, a rapid and intense coloration, and a viscosity which is advantageous for the microencapsulation. In this regard, the azaphthalides of this invention have the property that, on account of the long chain N-alkyl radical of Y', they remain colourless in the solutions of the above solvents, especially diisopropylnaphthalene or partially hydrogenated terphenyl, in a pH range from 4 to 10, and thus do not stain the aqueous phase, e.g. during encapsulation.

The capsule walls can be formed evenly around the droplets of the colour former solution by coacervation; and the encapsulating material can consist of gelatin and gum arabic, as described e.g. in U.S. Pat. No. 2,800,457. The capsules can also be formed preferably from an aminoplast or a modified aminoplast by polycondensation, as described in British patent specification Nos. 989 264, 1 156 725, 1 301 052 and 1 355 124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers of the formulae (1) to (3) can be used for the production of a wide variety of known kinds of pressure-sensitive copying material. The various systems differ substantially from one another in the arrangement of the capsules, of the colour reactants, i.e. the developers, and/or of the support. A preferred arrangement is that in which the encapsulated colour former is in the form of a layer on the back of a transfer sheet and the developer is in the form of a layer on the face of a receiver sheet.

Another arrangement of the components is that wherein the microcapsules which contain the colour former, and the developer, are in or on the same sheet, in the form of one or more individual layers, or are present in the paper pulp.

The capsules are preferably secured to the support by means of a suitable adhesive. As paper is the preferred support, these adhesives are principally paper-coating agents, for example gum arabic, polyvinyl alcohol, hydroxymethyl cellulose, casein, methyl cellulose, dextrin, starch or starch derivatives or polymer latices. These latter are e.g. butadiene/styrene copolymers or acrylic homopolymers or copolymers.

The paper employed comprises not only normal paper made from cellulose fibres, but also paper in which the cellulose fibres are replaced (partially or completely) by synthetic polymers.

The compounds of the formulae (1) to (3) can also be employed as developers in a thermoreactive recording material. This recording material usually contains at least one carrier, one colour former, one electron acceptor and, optionally, also a binder and/or waxes. Thermoreactive recording systems comprise, for example, heat-sensitive recording and copying materials and papers. These systems are used e.g. for recording information, for example in electronic computers, teleprinters or telewriters, or in recording and measuring instruments, e.g. electro-cardiographs. The image (mark) formation can also be effected manually with a heated pen. Laser beams can also be used to produce heat-induced marks.

The thermoreactive recording material can be composed such that the colour former is dispersed or dissolved in one binder layer and the developer is dissolved or dispersed in the binder in a second layer. Another possibility consists in dispersing both the colour former and the developer in one layer. By means of heat the binder is softened at specific areas and the colour former comes into contact with the developer (electron acceptor) at those points where heat is applied and the desired colour develops at once. Suitable developers are the same electron acceptors as are used in pressure-sensitive papers. Examples of developers are the clays already mentioned and especially phenolic resins, or also the phenolic compounds described e.g. in German Offenlegungsschrift No. 1 251 348, for example 4-tert-butylphenol, 4-phenylphenol, 4-hydroxydiphenyl ether, α-naphthol, β-naphthol, 4-hydroxymethylbenzoate, 4-hydroxyacetophenone, 2,2'-dihydroxydiphenyl, 4,4-isopropylidenediphenol, 4,4'-isopropylidene-bis-(2-methylphenol), 4,4'-bis-(hydroxyphenyl)valeric acid, 2,2'-methylene-bis-(4-phenylphenol), hydroquinone, pyrogallol, phloroglucinol, p-, m- and o-hydroxybenzoic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

Fusible, film-forming binders are preferably used for the manufacture of the thermoreactive recording material. These binders are normally water-soluble, whereas the azaphthalides and the developer are sparingly soluble or insoluble in water. The binder should be able to disperse and fix the colour former and the developer at room temperature.

By applying heat the binder softens or melts, so that the colour former comes in contact with the developer and a colour is able to form. Examples of binders which are soluble, or at least swellable, in water are e.g. hydrophilic polymers, for example polyvinyl alcohol, polyacrylic acid, hydroxyethyl cellulose, methyl cellulose, carboxymethyl cellulose, polyacrylamide, polyvinyl pyrrolidone, gelatin, starch or etherified corn starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose and polyvinyl carbazole. The preferred arrangement, however, is that in which the colour former and the developer are contained in one layer in a water-soluble binder.

The thermoreactive coatings can contain further ingredients. To improve the degree of whiteness, to facilitate the printing of papers, and to prevent the heated pen from sticking, the coatings can contain e.g. talcum, titanium dioxide, zinc oxide, aluminium hydroxide, calcium carbonate (e.g. chalk), clays or also organic pigments, for example urea/formaldehyde polymers. In order to effect the colour formation only within a limited temperature range, it is possible to add substances such as urea, thiourea, diphenyl thiourea, acetamide, acetanilide, stearyl amide, phthalic anhydride, metal stereates, phthalonitrile or other appropriate fusible products which induce the simultaneous melting of the colour former and the developer. Thermographic recording materials preferably contain waxes, e.g. carnauba wax, montana wax, paraffin wax, polyethylene wax or condensates of higher fatty acid amides and formaldehyde, or condensates of higher fatty acids and ethylenediamine.

The present invention also relates to a novel process for the preparation of azaphthalide compounds, which can be used as colour formers in pressure-sensitive or heat-sensitive recording materials.

In pressure-sensitive, carbon-free copier systems, an oily solution of the chromogenic dye intermediate, for example crystal violet lactone, benzoyl-leucomethylene blue, phthalides or fluoranes, is usually isolated in microcapsules which can be ruptured under pressure and which are presented either as a layer on a separate transfer sheet, so that a pair of independent copying sheets are formed, or are on the sensitised side of the copy-receiving sheet, so that a self-reactive sheet of paper is formed.

Crystal violet lactone (3,3-bis-(4'-dimethylaminophenyl)-6-dimethylaminophthalide) is usually employed as the chromogenic dye intermediate in such pressure-sensitive copier systems. As is known, a print produced with crystal violet lactone fades very rapidly under the influence of light, so that attempts are continually being made to find a suitable substitute.

Azaphthalides which contain an aminophenyl substituent and an indolyl substituent in the 3-position are good subtitutes which produce a satisfactory blue print with improved stability to light. However, the preparation of this colour-forming agent always results as stated above in a mixture of isomers of 4- and 7-azaphthalides. Although an improvement in light-fastness and at the same time also a decrease in the loss of reactivity (CB decline) can be achieved with these mixtures of isomers, undesirable discolouration (self-colouration) of the micro capsules containing the chromogenic substance usually occurs in the preparation of pressure-sensitive recording materials owing to the presence of the 7-azaphthalide isomer in the mixture of isomers.

It has now been found that an isomer-free 4-azaphthalide compound can be obtained if the reaction of quinolinic anhydride with the indole compound for the preparation of the isomer-free keto-acid required as an intermediate is carried out in a specific organic reaction medium and in the presence of a metal salt of a polyvalent metal.

The present invention accordingly relates to a process for the preparation of 4-azaphthalide compounds of the formula

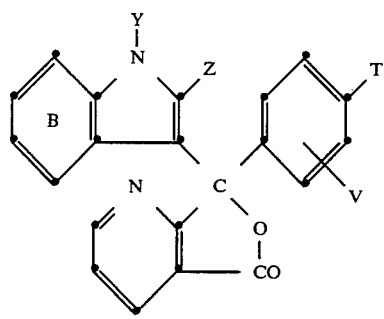

(1a)

in which Y is hydrogen, $C_1$–$C_{12}$ alkyl which is unsubstituted or substituted by halogen, cyano, hydroxyl or lower alkoxy, acyl having 1 to 12 carbon atoms, benzyl or benzyl which is substituted by halogen, nitro, lower alkyl or lower alkoxy, Z is hydrogen, lower alkyl or phenyl, T is —$OR_1$ or, preferably

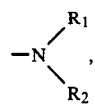

wherein $R_1$ and $R_2$ independently of each other are hydrogen, $C_1$–$C_{12}$ alkyl which is unsubstituted or substituted by halogen, cyano, hydroxyl or lower alkoxy, cycloalkyl, phenyl, benzyl or phenyl or benzyl which is substituted by halogen, nitro, cyano, lower alkyl, lower alkoxy or lower alkoxycarbonyl, or $R_1$ and $R_2$, together with the connecting nitrogen atom, are a 5-membered or 6-membered, preferably saturated heterocyclic radical and V is hydrogen, halogen, hydroxyl, nitro, lower alkyl or lower alkoxy, and in which the ring B is unsubstituted or substituted by halogen, nitro, cyano, lower alkyl, lower alkoxy, lower alkoxycarbonyl, amino, mono-(lower alkyl)amino or di-(lower alkyl)-amino.

The process comprises reacting quinolinic anhydride with an indole compound of the formula

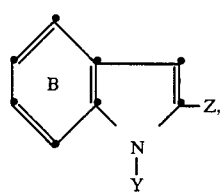

(7a)

in which B, Y and Z are as defined, in the presence of an inorganic or organic metal salt of a polyvalent metal in an organic reaction medium consisting of a lower aliphatic monocarboxylic acid or a nitrile of this acid at a temperature of not more than 65° C., further condensing the resulting reaction product with a compound of the formula

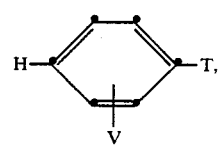

(5a)

in which T and V are as defined, and adjusting the pH value of the reaction mixture to not less than 6.

In the definition of the radicals of the 4-azaphthalide, lower alkyl and lower alkoxy are as a rule groups or moieties of groups having 1 to 5, in particular 1 to 3 carbon atoms. Examples of lower alkyl groups are methyl, ethyl, n-propyl, isopropyl, n-butyl, sec.-butyl or amyl; and examples of lower alkoxy groups are methoxy, ethoxy or isopropoxy.

Acyl is, in particular, formyl, lower alkylcarbonyl, for example acetyl or propionyl, or benzoyl. Other acyl radicals can be lower alkylsulfonyl, for example methylsulfonyl or ethylsulfonyl, and phenylsulfonyl. Benzoyl and phenylsulfonyl can be substituted by halogen, methyl, methoxy or ethoxy.

An alkyl group $R_1$, $R_2$ or Y can be a straight-chain or branched alkyl radical. Examples of such alkyl radicals are methyl, ethyl, n-propyl, isopropyl, n-butyl, sec.-butyl, amyl, n-hexyl, 2-ethylhexyl, n-heptyl, n-octyl, iso-octyl, n-nonyl, isononyl and n-dodecyl.

A substituted alkyl radical $R_1$, $R_2$ or Y is, in particular, cyanoalkyl, halogenoalkyl, hydroxyalkyl or alkoxyalkyl, in each case preferably having a total of 2 to 4 carbon atoms, for example $\beta$-cyanoethyl, $\beta$-chloroethyl, $\beta$-hydroxyethyl, $\beta$-methoxyethyl or $\beta$-ethoxyethyl.

Examples of preferred substituents on a benzyl group $R_1$, $R_2$ or Y or a phenyl group $R_1$ or $R_2$ are halogens, nitro, methyl and methoxy. Examples of such araliphatic or aromatic radicals are p-methylbenzyl, o- and p-chlorobenzyl, o- and p-nitrobenzyl, o- and p-tolyl, xylyl, o-, m- or p-chlorophenyl, o- and p-nitrophenyl and o- and p-methoxyphenyl.

Examples of heterocyclic radicals formed by the substituents $R_1$ and $R_2$ together with the common nitrogen atom are pyrrolidino, piperidino, pipecolino, morpholino, thiomorpholino and piperazino, for example N-methylpiperazino. Preferred heterocyclic radicals are piperidino, morpholino and especially pyrrolidino.

T is preferably the amino group of the formula —$NR_1R_2$.

V is preferably in the m-position relative to the substituent T.

The substituents $R_1$ and $R_2$ can be different, but are preferably identical. Preferably, $R_1$ and $R_2$ are benzyl or lower alkyl, especially methyl or ethyl.

V is preferably hydrogen, methyl, methoxy or, in particular, ethoxy.

The N-substituent Y is preferably benzyl, acetyl, propionyl or, in particular, alkyl having 1 to 8 carbon atoms, for example n-octyl, n-butyl, methyl or ethyl. A particularly preferred N-substituent Y is ethyl or especially n-octyl. Z is preferably phenyl or, in particular, methyl, The benzene ring B is preferably not further substituted or is substituted by halogen.

Examples of halogen are fluorine, bromine and, preferably, chlorine.

In carrying out the process according to this aspect of the invention, the substances participating in the reaction are preferably each employed in molar amounts.

The azaphthalide compounds of the formula (1a) are prepared continuously in two steps without isolation of the intermediate formed as reaction product.

The first step, in wich quinolinic anhydride is reacted with the indole compound of the formula (7a) in organic solvents of the type defined and in the presence of an organic or inorganic metal salt, is advantageously carried out at a temperature of 0° to 50° C., preferably at room temperature (17° to 30° C.).

The reaction time depends on the temperature, the metal salt used as the catalyst and the solvent, and is generally between ½ and 10 hours, preferably 2 and 6 hours.

The lower aliphatic monocarboxylic acid used as the reaction medium in the process according to the invention is advantageously a carboxylic acid which is liquid under the reaction conditions, and can have 1 to 5 carbon atoms.

Suitable aliphatic monocarboxylic acids which form the reaction medium are formic acid, acetic acid, dichloroacetic acid, propionic acid, butyric acid, isobutyric acid and valeric acid, and mixtures of these acids.

Examples of corresponding nitriles which can likewise be used as the reaction medium in the process according to the invention are acetonitrile, propionitrile and butyronitrile.

However, preferred solvents are aliphatic monocarboxylic acids having 2 to 4 carbon atoms, for example butyric acid, isobutyric acid, propionic acid and, in particular, acetic acid, and mixtures of these carboxylic acids.

The metal salts used according to the invention are advantageoulsy derived from polyvalent metals of atomic weight 24 to 210, preferably 26 to 140 and in particular 26 to 120. Examples of such metals are aluminium, barium, lead, cadmium, calcium, chromium, iron, gallium, cobalt, copper, magnesium, manganese, molybdenum, nickel, mercury, strontium, tantalum, titanium, vanadium, tungsten, zinc, tin and zirconium. Aluminium, calcium, cadmium, iron, chromium, cobalt, copper, nickel, manganese, strontium, tin and zinc are preferred. The anionic component of these metal salts is advantageously derived from mineral acids or from organic acids, and is, for example, a sulfate, halide, nitrate, formiate, acetate, propionate, citrate or stearate.

A halide can be a fluoride, iodide, bromide or, preferably, chloride, as well as a pseudohalide, such as a thiocyanate.

The metal salts can be used individually or as mixtures.

Preferred metal salts are sulfates or, in particular, halides of metals from the group comprising aluminium, calcium, iron, cadmium, cobalt, copper, manganese, nickel, tin and zinc, for example aluminium chloride, calcium chloride, nickel chloride, cobalt chloride, iron chloride, copper chloride, zinc chloride, tin chloride, tin bromide, manganese chloride, nickel bromide, calcium fluoride and cadmium iodide and mixtures thereof. In general, the best results are achieved in the presence of chlorides of aluminium, calcium, cobalt, iron, copper or zinc. Zinc chloride and aluminium chloride are of particular interest. A mixture of calcium chloride and zinc chloride, preferably in a ratio of 1:9 to 2:1, is also preferred.

The amount of metal salt in the first reaction stage is advantageously 10 to 100 mol %, preferably 12 to 50 mol %, based on the quinolinic anhydride used.

When the first reaction stage has ended, the reaction product (keto-acid, which is not isolated) is further condensed directly with the compound of the formula (5a). This second reaction stage is preferably carried out by reacting the components in the presence of an acid dehydrating agent at a temperature of 20° to 80° C. Examples of such condensing agents are sulfuric acid, phosphoric acid, phosphorus oxychloride and, in particular, acetic anhydride. If acetic anhydride is used, temperatures between 20° und 60° C. are preferred. The reaction time of the second step is generally 1 to 4 hours, preferably 1½ to 3 hours.

Finally, the pH value of the reaction mixture is adjusted to not less than 6. For this purpose it is convenient to use alkalis such as alkali metal hydroxides, for example sodium or potassium hydroxide, ammonia or an alkali metal carbonate or bicarbonate, as well as mixtures of these compounds. The pH value is preferably adjusted to 7 to 11.

The final product of the formula (1a) is isolated in generally known manner by removal of the precipitate washing and drying, or by treatment with suitable organic solvents, for example methanol, ethanol or isopropanol and if necessary recrystallisation of the product.

If $OR_1$ and/or V in the reaction product of the formula (1a) are hydroxyl, the hydroxyl group can be subsequently alkylated or aralkylated as defined for $R_1$ and V.

Alkylation or aralkylation of the reaction products in which V and/or $OR_1$ are hydroxyl is generally carried out by known processes. For example, the reaction is carried out in the presence of an acid acceptor, for example an alkali metal carbonate or a tertiary nitrogen base, such as triethylamine, if necessary in the presence of an inert organic solvent, for example acetone, isopropyl alcohol, chlorobenzene or nitrobenzene. The alkylating and aralkylating agents may be the same as those indicated for the preparation of azaphthalides compounds of formulae (1) to (3).

A particularly advantageous embodiment of the novel process comprises dissolving or suspending quinolinic anhydride in a saturated aliphatic $C_2$-$C_4$-monocarboxylic acid, in particular acetic acid, or also in acetonitrile, adding an indole compound of the formula (7a) and stirring the mixture at room temperature in the presence of an inorganic metal salt, in particular a metal halide, of a polyvalent metal or atomic weight 26 to 66, for example zinc chloride, calcium chloride, aluminium chloride, iron chloride, cobalt chloride or copper dichloride, preferably for 2 to 6 hours. The compound of the formula (5a) is then added and, after addition of acetic anhydride, the reaction mixture is heated at 30° to 60° C., preferably for 1 to 3 hours. The pH is then adjusted to 7.5 to 9 for example with an alkali metal hydroxide or aqueous ammonia. The precipitated 4-azaphthalide compound of the formula (1a) is isolated and, if necessary, recrystallised.

The preferred 4-azaphthalide compounds of the formula (1a), which are prepared continuously by the continuous process of the invention, are those in which V is hydrogen, methyl, hydroxyl, methoxy or, in particular, ethoxy and T is a group of the formula $—NR_1R_2$, in which $R_1$ and $R_2$ are methyl or ethyl, or $—NR_1R_2$ is pyrrolidino or piperidino. Y is preferably alkyl having 1 to 8 carbon atoms, Z is, in particular, methyl and the ring B is preferably unsubstituted. The most preferred azaphthalide compounds of the formula (1a) are those in which the group

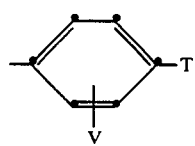

is 2-ethoxy-4-dimethylaminophenyl or 2-ethoxy-4-diethylaminophenyl, Y is ethyl or especially octyl and Z is methyl, and the ring B is unsubstituted.

A material advantage of the process of the present invention is that it can easily be applied industrially, and that it gives pure final products in very good yields without isolation of the keto-acids formed as intermediates. In particular, 4-azaphthalide compounds which are completely free from the corresponding 7-azaphthalide isomers of the formula

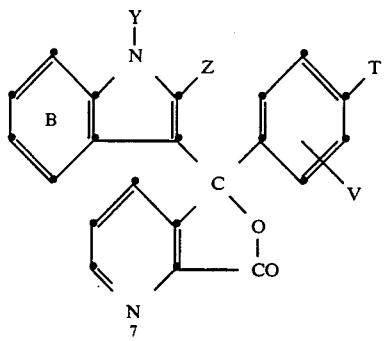

are obtained.

The 4-azaphthalide compounds of the formula (1a) prepared by the process according to the invention are usually colourless or at most faintly coloured. They are particularly suitable as rapidly developing colour forming agents for use in a heat-sensitive or, in particular, pressure-sensitive recording material, which can also be a copying material. When these colour formers are brought into contact with a developer, which is preferably acid, i.e. an electron acceptor, there result intense green-blue, blue or violet-blue colour shades which are fast to sublimation and light both on clays and, in particular, on phenolic substrates.

Compared with the mixture of isomers of 4- and 7-azaphthalides known hitherto from German Offenlegungsschrift No. 2,842,263 or German Offenlegungsschrift No. 3,116,815, according to which lather publication the troublesome 7-azaphthalide compound is reduced to a content of 2%, the isomer-free 4-azaphthalides prepared according to the invention have the advantage that they do not cause undesirable premature discolouration (self-colouration) during preparation or storage of the recording materials.

The invention is illustrated by the following Examples, in which the percentages are by weight, unless otherwise indicated.

EXAMPLE 1

20.0 g of quinolinic anhydride, 80 ml of acetic acid, 20.3 g of N-ethyl-2-methylindole and 2.74 g of zinc chloride are stirred at 20° C. for 5 hours. 23.6 g of 3-(N,N-diethylamino)-phenetole and 30 ml of acetic anhydride are then added, after which the reaction mixture is warmed to 50° to 60° C. and stirred at this temperature for 2 hours. After addition of 170 ml of 30% aqueous ammonia and 100 ml of water, the product precipitates as a paste and is isolated. 160 ml of isopropanol are added to the paste and the mixture is refluxed for 1 hour. After cooling, the recrystallised product is filtered off, washed with isopropanol and dried, affording 46.9 g of the isomer-free 4-azaphthalide compound of the formula

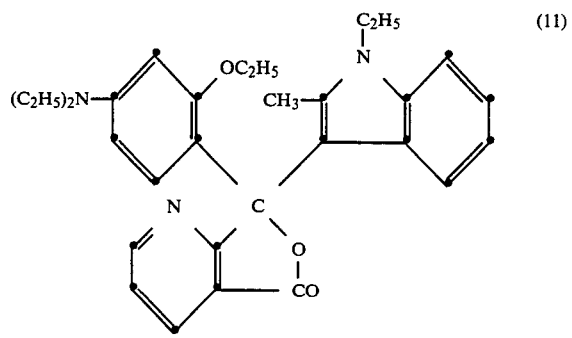

of melting point 156° to 158° C.

EXAMPLE 2

6.0 g of quinolinic anhydride, 9.5 g of N-octyl-2-methylindole and 0.56 g of zinc chloride are stirred in 30 ml of glacial acetic acid at 20° C. for 5 hours. 6.6 g of 3-diethylaminophenetole and 8 ml of acetic anhydride are then added, after which the mixture is stirred at 50° C. for 2½ hours. The product is precipitated with 30% aqueous ammonia, separated from the aqueous phase and recrystallised from isopropanol, affording 16.5 g of the isomer-free 4-azaphthalide compound of the formula

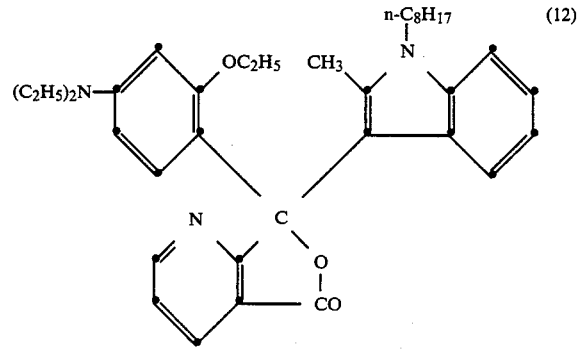

of melting point 113°–118° C.

The procedure described in the example is repeated, using 0.30 g of copper-II dichloride or 0.53 g of aluminium trichloride instead of 0.56 of zinc chloride. Yield: 15.9 g or 16.8 g of the 4-azaphthalide compound of the formula (12) of melting point 113°–116° C. or 115°–119° C.

EXAMPLE 3

1.5 g of quinolinic anhydride, 2.3 g of N-octyl-2-methylindole, 10 ml of glacial acetic acid and a mixture of 0.11 g of calcium chloride and 0.14 g of zinc chloride are stirred at 20° C. for 5 hours. 1.6 g of 3-diethylaminophenetole and 2 ml of acetic anhydride are then added, after which the reaction mixture is stirred at 50° C. for 2½ hours. The product is precipitated with 30% aqueous ammonia, separated from the aqueous phase and recrystallised from isopropanol, affording 3.8 g of the isomer-free 4-azaphthalide compound of the formula (12) of melting point 114°–117° C.

The procedure described in this example is repeated, using 0.19 g of iron trichloride or 0.14 g of cobalt dichloride instead of the indicated metal salt mixture. Yield: 3.3 g or 3.8 g or the 4-azaphtahlide compound of the formula (12) of melting point 113°–117° C. or 113°–116° C.

EXAMPLE 4

8 g. of quinolinic anhydride, 1.1 g of zinc chloride, 40 ml of acetic acid and 9.95 g of N-butyl-2-methylindole are stirred at 20°–23° C. for 5 hours. Then 9.3 g of 3-(N,N-diethylamino)-phenetole and 7.5 ml of acetic anhydride are added, and the reaction mixture is stirred at 50°–60° C. for 2 hours. When the reaction is complete, the acetic acid solution is neutralised with 30% aqueous ammonia, whereupon the product precipitates. After separation from the aqueous phase, the crude product is dissolved in glacial acetic acid, again precipitated with 30% aqueous ammonia and recrystallised from ethanol affording 16.8 g of the isomer-free 4-azaphthalide compound of the formula

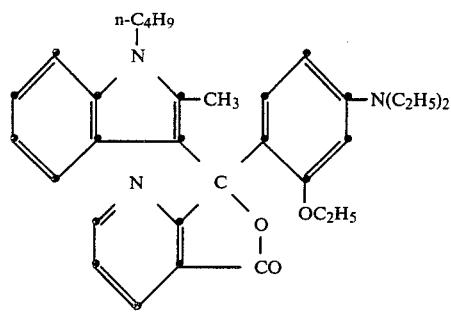

(13)

of melting point 152°–154° C.

EXAMPLE 5

60 g of quinolinic anhydride and 116 g of 1-n-octyl-2-methylindole are stirred for 3¾ hours at 65°–70° C. in 100 ml of toluene. The reaction mixture is then evaporated to dryness and the residue is dissolved at 70° C. in 2 liters of ethanol. The solution is cooled to 0° C. and the product precipitates. The precipitate is isolated by filtration, washed with ethanol and petroleum ether and dried in vacuo at 60° C., affording 90 g (57% of theory) of a mixture of isomers consisting of the compounds of the formulae

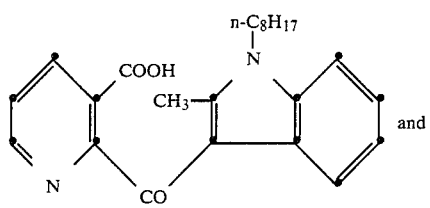

(14a)

and

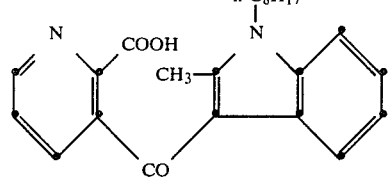

(14b)

Melting point of the mixture: 105°–112° C.

39.3 g of this mixture of isomers and 19.3 g of 3-diethylaminophenetol are stirred in 130 ml of acetic anhydride for 3½ hours at 60°–65° C. The reaction mixture is then poured into 1 liter of water and the pH is adjusted to 8 by stirring in 30% sodium hydroxide solution. The precipitated oil is separated and dissolved in toluene. The toluene solution is dried over sodium sulfate and concentrated. The oily residue is chromatographed through a column of alumina with a 1:1 mixture of chloroform and methanol. Yield: 30 g (53% of theory) of a mixture of azaphthalides isomers consisting of compounds of the formulae

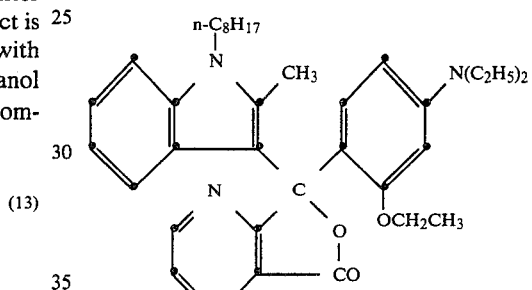

(15a)

and

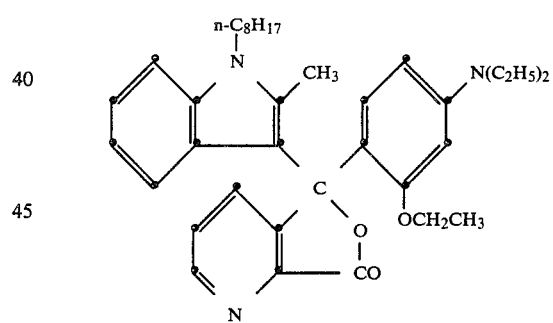

(15b)

with a melting point of 119°–121° C. This colour former develops a blue colour on phenolic resin.

Mixtures of isomers of the azaphthalides of the formulae

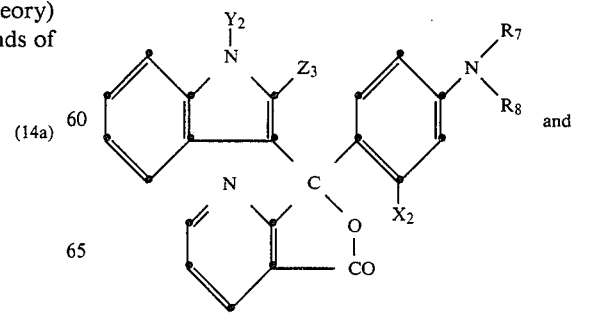

(16a)

and

-continued

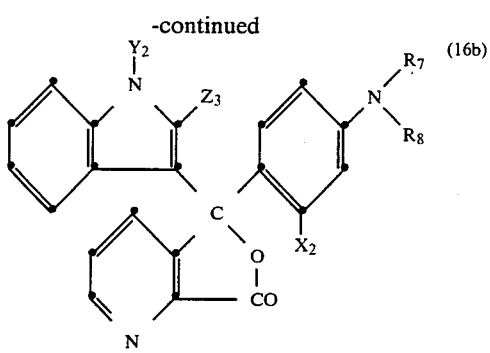

are obtained in the same manner as described in Example 5, using the corresponding starting materials.

veloper. The first sheet containing the microcapsules and the paper coated with colour developer are placed on top of one another with the coated sides face to face. A pressure-sensitive copying paper which does not discolour even on storage is obtained. Pressure is exerted on the first sheet by writing by hand or with a typwriter, and an intense blue copy of excellent light fastness develops immediately on the sheet coated with the developer.

Corresponding non-discoloured pressure-sensitive copying paper and intense, light-fast blue copies produced by writing are also obtained using any of the other colour formers obtained in Examples 2, 3 and 4.

EXAMPLE 17

A solution of 3 g of the mixture of isomers of the

TABLE

| Example | $-N\begin{matrix}R_7\\R_8\end{matrix}$ | $X_2$ | $Y_2$ | $Z_3$ | p./°C. | Colour on phenolic resin |
|---|---|---|---|---|---|---|
| 6 | $-N(C_2H_5)_2$ | $-OC_2H_5$ | $-n-C_6H_{13}$ | $-CH_3$ | 134–136 | blue |
| 7 | $-N(CH_3)_2$ | H | $-n-C_8H_{17}$ | $-CH_3$ | 126–128 | blue |
| 8 | $-N(C_2H_5)_2$ | $-OC_2H_5$ | $-n-C_7H_{15}$ | $-CH_3$ | 109–113 | blue |
| 9 | $-N(C_2H_5)_2$ | $-OC_2H_5$ | $-n-C_9H_{19}$ | $-CH_3$ | 105–107 | blue |
| 10 | $-N(C_2H_5)_2$ | $-OCH_2-\text{phenyl}$ | $-n-C_8H_{17}$ | $-CH_3$ | 166–167 | blue |
| 11 | $-N\text{(pyrrolidino)}$ | $-OC_2H_5$ | $-n-C_6H_{13}$ | $-CH_3$ | 146–148 | blue |
| 12 | $-N\text{(pyrrolidino)}$ | $-OC_2H_5$ | $-n-C_7H_{15}$ | $-CH_3$ | 151–153 | blue |
| 13 | $-N\text{(pyrrolidino)}$ | $-OC_2H_5$ | $-n-C_8H_{17}$ | $-CH_3$ | 147–148 | blue |
| 14 | $-N\text{(pyrrolidino)}$ | $-OC_2H_5$ | $-n-C_9H_{19}$ | $-CH_3$ | 115–118 | blue |
| 15 | $-N(CH_3)-\text{cyclohexyl}$ | $-OC_2H_5$ | $-n-C_8H_{17}$ | $-CH_3$ | 117–119 | blue |

Preparation of a pressure-sensitive copying paper

EXAMPLE 16

A solution of 3 g of the 4-azaphthalide compound of the formula (11), obtained in Example 1, in 80 g of diisopropylnaphthlene and and 17 g of kerosene is microencapsulated by coacervation in a manner which is known per se with gelatin and gum arabic, after which no discolouration of the microcapsules occurs. The microcapsules are mixed with starch solution and brushed onto a sheet of paper. A second sheet of paper is coated on the face with phenolic resin as colour deazaphthalides of the formulae (15a) and (15b) obtained in Example 5 in 80 g diisopropylnaphthalene and 17 g of kerosene are microencapsulated by coacervation in a manner known per se with gelatin and gum arabic. The microcapsules are mixed with starch solution and coated on a sheet of paper. The face of a second sheet of paper is coated with phenolic resin as colour developer. The first sheet and the sheet coated with the developer are laid on top of each with other with the coated sides face to face. Pressure is exerted on the first sheet by writing by hand or typewriter and an intense blue copy of excellent lightfastness develops immediately on the sheet coated with the developer.

Correspondingly intense and lightfast blue copies are also obtained by using each of the other colour formers as obtained in Preparatory Examples 6 to 15.

EXAMPLE 18

1 g of the mixture of isomers of the azaphthalides of the formulae (15a) and (15b) is dissolved in 17 g of toluene. With stirring, 12 g of polyvinyl acetate, 8 g of calcium carbonate and 2 g of titanium dioxide are added to this solution. The resultant suspension is diluted with toluene in the weight ratio 1:1 and applied to a sheet of paper with a knife to a thickness of 10 μm. On this sheet of paper is laid a second sheet, the underside of which has been coated to a weight of 3 g/m² with a mixture consisting of 1 part of an amide wax, 1 part of a stearic wax and 1 part of zinc chloride. Pressure is exerted on the top sheet by hand or typewriter and an intense and lightfast blue copy develops immediately on the sheet coated with the colour former.

Preparation of a heat-sensitive recording material

EXAMPLE 19

In a ball mill, 32 g of 4,4′-isopropylidenediphenol (bisphenol A), 3.8 g of the distearylamide of ethylenediamine, 39 g of kaolin, 20 g of an 88% hydrolysed polyvinyl alcohol and 500 ml of water are ground to a particle size of about 5 μm. In a second ball mill, 6 g of the mixture of isomers of the azaphthalides of the formulae (15a) and (15b) of Example 5, 3 g of a 88% hydrolysed polyvinyl alcohol and 60 ml of water are ground to a particle size of about 3 μm.

Both dispersions are mixed and applied to paper to a dry coating weight of 5.5 g/m². An intense blue colour of excellent fastness to light and sublimation is produced by contacting the paper with a heated ball-point pen.

Intense and lightfast blue colorations are also obtained by using each of the other colour formers of Examples 2 to 15.

EXAMPLE 20

In a ball mill, 2.7 g of the mixture of isomers of the azaphthalides of the formulae (15a) and (15b), 24 g of N-phenyl-N′-(1-hydroxy-2,2,2-trichloroethyl)urea, 16 g of stearylamide, 59 g of an 88% hydrolysed polyvinyl alcohol and 58 ml of water are ground to a particle size of 2-5 μm. This suspension is applied to a sheet of paper to a dry coating weight of 5.5 g/m². An intense and lightfast blue colour is obtained by contacting the paper with a heated ball-point pen.

What is claimed is:

1. A pressure-sensitive or heat-sensitive recording material which comprises a support which contains or has coated thereon as color former at least one chromogenic azaphthalide of the formula

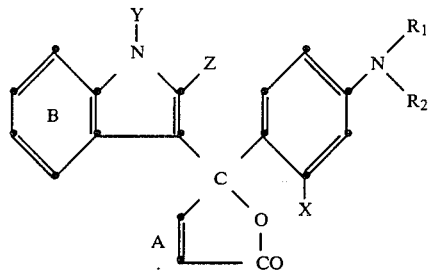

wherein
- R$_1$ and R$_2$ independently of each other are hydrogen, C$_1$-C$_{12}$alkyl which is unsubstituted or substituted by halogen, hydroxyl, cyano or lower alkoxy, or are cycloalkyl, benzyl or phenyl, or benzyl or phenyl which are substituted by halogen, nitro, cyano, lower alkyl, lower alkoxy or lower alkoxycarbonyl;
- or R$_1$ and R$_2$ together with the nitrogen atom to which they are attached are pyrrolidinyl;
- X is hydrogen, halogen, lower alkyl, lower alkoxy, benzyl, phenyl, benzyloxy, phenoxy, or benzyl or benzyloxy which are substituted by halogen, nitro, lower alkyl or lower alkoxy;
- Y is C$_6$-C$_9$alkyl;
- Z is hydrogen, lower alkyl or phenyl; and
- the ring A is a pyridine radical and
- the benzene nucleus B is unsubstituted or substituted by halogen, cyano, nitro, lower alkyl, lower alkoxy, lower alkoxycarbonyl, amino, lower alkylamino or di-(lower alkyl)-amino.

2. A pressure-sensitive recording material of claim 1, wherein the azaphthalide is dissolved in an organic solvent, and which recording material further comprises at least one solid electron acceptor.

3. A pressure-sensitive recording material of claim 2, wherein the azaphthalide is encapsulated in microcapsules.

4. A pressure-sensitive recording material of claim 3, wherein the encapsulated azaphthalide is present in the form of a layer on the back of a transfer sheet and the electron acceptor is present in the form of a layer on the face of a receiving sheet.

5. A pressure-sensitive recording material of claim 1, which comprises the azaphthalide together with one or more other colour formers.

6. A heat-sensitive recording material of claim 1, which comprises in at least one layer, at least one azaphthalide colour former, at least one electron acceptor and at least one binder.

7. A pressure-sensitive recording material of claim 1, wherein R$_1$ is lower alkyl, cyclohexyl or benzyl and R$_2$ is lower alkyl or benzyl.

8. A pressure-sensitive recording material of claim 1, wherein X is hydrogen, benzyloxy or lower alkoxy.

9. A pressure-sensitive recording material of claim 1 of the formula

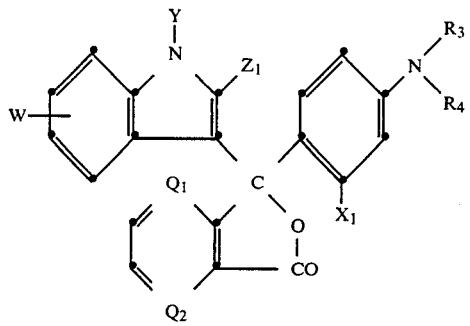

wherein $R_3$ and $R_4$ independently of each other are lower alkyl, benzyl or benzyl which is substituted by halogen, methyl or methoxy, or $R_3$ and $R_4$ together with the nitrogen atom to which they are attached are pyrrolidinyl; one of $Q_1$ and $Q_2$ is nitrogen and the other is CH; $X_1$ is hydrogen, lower alkoxy or benzyloxy; Y is $C_6$–$C_9$alkyl; $Z_1$ is lower alkyl or phenyl; and W is hydrogen or halogen.

10. A pressure-sensitive recording material of claim 9, wherein each of $R_3$ and $R_4$ is lower alkyl or benzyl, or $R_3$ and $R_4$ together with the nitrogen atom to which they are attached are pyrrolidinyl, $Z_1$ is methyl or phenyl, Y is $C_6$–$C_8$alkyl and W is hydrogen.

11. A pressure-sensitive recording material of claim 10, wherein $X_1$ is lower alkoxy.

12. A pressure-sensitive recording material of claim 10, wherein $R_3$ and $R_4$ are methyl or ethyl, $X_1$ is ethoxy, $Z_1$ is methyl and Y is n-octyl.

13. A pressure-sensitive recording material of claim 10, wherein $R_3$ and $R_4$ are ethyl, $X_1$ is ethoxy, Z is methyl, Y is octyl, $Q_1$ is N and $Q_2$ is CH.

* * * * *